United States Patent [19]

Calenoff et al.

[11] Patent Number: 4,844,966
[45] Date of Patent: Jul. 4, 1989

[54] ASSAYING TOTAL IGE LEVELS WITH FLUOROGENIC ENZYME LABELED ANTIBODY

[75] Inventors: Emanuel Calenoff, Burlingame; Tsay Yuh-Geng, San Jose; Ruth M. Jones, Los Altos; John R. Scott, Mountain View, all of Calif.

[73] Assignee: Minnesota Mining and Manufacturing Company, St. Paul, Minn.

[21] Appl. No.: 144,738

[22] Filed: Jan. 15, 1988

Related U.S. Application Data

[63] Continuation of Ser. No. 476,451, Mar. 17, 1983, abandoned, which is a continuation-in-part of Ser. No. 462,585, Jan. 31, 1983, abandoned, which is a continuation-in-part of Ser. No. 444,622, Nov. 26, 1982, abandoned, which is a continuation-in-part of Ser. No. 434,061, Oct. 13, 1982, abandoned.

[51] Int. Cl.$^4$ ............................................. G01N 33/53
[52] U.S. Cl. .......................................... 435/7; 435/21; 436/513; 436/809
[58] Field of Search ..................... 436/513, 809; 435/7, 435/21

[56] References Cited

U.S. PATENT DOCUMENTS

| | | | |
|---|---|---|---|
| 4,002,532 | 1/1977 | Weltman | 436/513 |
| 4,240,751 | 12/1980 | Linnecke | 435/291 X |
| 4,376,110 | 3/1983 | David | 436/548 |
| 4,444,880 | 4/1984 | Tom | 436/530 X |
| 4,501,970 | 2/1985 | Nelson | . |

FOREIGN PATENT DOCUMENTS 83306178.1 10/1982 European Pat. Off. .

OTHER PUBLICATIONS

Chemical Abstracts, 92:39735t (1980).
"Enzyme-Immunoassay", Maggio, E. T., ed., pp. 26, 173–178, 186, CRC Press, Inc., Boca Raton, 1980.
Shalev, A., et al.; J. Immunol. Methods, 38:125–139 (1980).
Voller, A., et al.; Brief Communication, WHO 51:209–211 (1974).
Hellsing, K., et al., Chapt. 3, pp. 67–112 Automated Immunoanalysis (Marcel Dekker, New York).
Ceska, M., et al., Eur. J. Immunol. 2:58–62 (1972).
Butler, J. E., Chapt. 2 "Antibody–Antigen and Antibody–Hapten Reactions", pp. 5–52 in *Enzyme Immunoassay*, (E. Maggio, Ed CRC Press Boca Raton, Fla. 1980).
Clark, B. et al., Chapt. 8 "Enzyme Linked Immunosorbent Assay (ELISA): Theoretical and Practical Aspects" pp. 167–179 in *Enzyme Immunoassay* (E. Maggio, Ed. CRC Press Boca Raton, Fla. (1980).
Mattiasson; B., et al., Chapt. 11, "Novel Approaches to Enzyme Immunoassay" pp. 213–248 in *Enzyme Immunoassay* (E. Maggio, Ed CRC Press Boca Raton, Fla. 1980).
Savory, J., et al., Chapt. 16, pp. 335–343 in Automated Immunoanalysis Part 2 (R. Ritchie, and Marcel Dekker, Inc. New York 1978).

*Primary Examiner*—Christine M. Nucker
*Attorney, Agent, or Firm*—Donald M. Sell; Walter N. Kirn; Philip M. Goldman

[57] ABSTRACT

A method for identifying and quantifying total IgE levels in patient serum by conjugating the IgE in the serum with anti-IgE antibody adhering to an insoluble support, conjugating the serum IgE with an enzyme labeled anti-IgE antibody, contacting the enzyme label with a solution of a substrate which will yield a fluorescent product in the presence of the enzyme, and measuring the level of fluoresence in the solution. Special reagents and their manufacture are also disclosed.

14 Claims, No Drawings

4,844,966

ASSAYING TOTAL IGE LEVELS WITH FLUOROGENIC ENZYME LABELED ANTIBODY

RELATIONSHIP TO COPENDING APPLICATIONS

This is a continuation of application Ser. No. 476,451 filed Mar. 17, 1983, abandoned, which is application is a continuation-in-part of applications Ser. Nos. 462,585 filed Jan. 31, 1983, abandoned, 444,622 filed Nov. 26, 1982, now abandoned, and 434,061 filed Oct. 13, 1982, abandoned.

FIELD OF THE INVENTION

This invention relates to methods and reagents for assaying blood serum of patients demonstrating allergic symptomatology to measure the total IgE level in the serum. In particular, this invention relates to diagnostic methods and reagents for measuring total IgE levels with increased speed and accuracy, the results of which can be reliably used in evaluating for allergic disease and identifying the different allergens to which an individual may be sensitive.

BACKGROUND OF THE INVENTION

DESCRIPTION OF THE PRIOR ART

Radiometric and fluorometric methods for identifying and measuring allergy specific IgE levels in patient serum are commercially available and are known as the RAST test, for example. U.S. Pat. Nos. RE-29,474; 3,555,143; 3,648,346; 3,720,760 and 3,966,898 relate to these methods and reagents therefor. Enzymatic immunological methods for identifying and quantifying antigens and antibodies in liquids are widely used and are known as the ELISA and EIA, for example. Basic technology for enzymatic assays and reagents therefor is disclosed in U.S. Pat. Nos. RE-29,169 and 3,839,153, for example. Total human IgE tests such as the PHADEBAS IgE PRIST® radioimmunoassay test (Pharmacia) and TANDEM ™ radioimmunoassay test (Hybritech) are known.

A review of the current state of the art with regard to immunoassays for the detection of proteins in solutions is provided by R. Rose et al, *Manual of Clinical Immunology*, 2nd ed. American Society for Microbiology, Washington, pp 327–429, 775–849 (1980) and by A. Voller et al, *Immunoassays for the 80's*, University Park Press, Baltimore (1981), and the publications cited therein, the entire contents of both publications being hereby incorporated by reference. The chapter therein by T. A. E. Platts-Mills et al, "Radioimmunoassays in Allergy", pp 289–311, and the publications cited therein provide a comprehensive review of the field of this invention.

Procedures for binding proteins to insoluble supports have been primarily described. Antibodies have also been covalently bonded to insoluble supports as described in U.S. Pat. Nos. 3,551,555, 3,553,310, 4,048,298 and RE-29,474. Binding of antibodies to polystyrene by adsorption has been described in U.S. Pat. Nos. 3,646,346 and 4,092,408, for example. Allergens have been covalently bonded to a variety of insoluble supports as described in U.S. Pat. No. 3,720,760.

Polyethylene glycol has been used in protein fractionation processes as described by A. Polson et al, *Biochim. Biophys Acta*, vol. 82, pp 463–475 (1964) and A. Polson et al, *Vox Sang*, vol. 23, pp. 107–118 (1972).

SUMMARY OF THE INVENTION

This invention relates to a method for quantifying total IgE levels in patient serum. It comprises the steps of first contacting an insoluble support having an anti-IgE antibody adhering thereto with patient serum for a sufficient time to permit conjugation of anti-IgE antibody with IgE in the patient serum. The patient serum is then removed from the support. Secondly, the insoluble support is contacted with an enzyme labeled anti-IgE antibody for sufficient time to permit conjugation of serum IgE bound to the insoluble support with the enzyme labeled anti-IgE antibody. A fluorogenic enzyme, as used herein, is defined as an enzyme by means of which suitable substrate will undergo chemical reaction to yield fluorescent products. The unconjugated enzyme labeled anti-IgE antibody is then removed from the support. Thirdly, the insoluble support is contacted with a solution of a substrate which undergoes chemical reaction to yield a fluorescent product when in the presence of the fluorogenic enzyme, the contact being continued for a sufficient time to yield fluorescent product. The level of fluorescence in the solution is then measured.

In the insoluble anti-IgE antibody reagent of this invention the anti-IgE antibody can be adherent to the insoluble support by covalent or non-covalent bonding such as by absorption or adsorption, for example. The anti-IgE antibody adhering to the insoluble support is preferably stabilized with a polysaccharide-animal protein complex prepared by treating the surface of the insoluble support to which the anti-IgE antibody is bound with an aqueous solution of saccharide and animal protein before drying. The anti-IgE antibody is preferably adherent to the insoluble support by non-covalent bonding.

In certain preferred embodiments of this invention, the insoluble support has a plurality of test wells separated by opaque material, the anti-IgE antibody adherent to the insoluble support and the enzyme labeled anti-IgE antibody are monoclonal antibodies, the enzyme is alkaline phosphatase, the enzyme labeled anti-IgE is contacted with the insoluble support in an aqueous solution containing from 1 to 8 weight percent polyethylene glycol having a molecular weight of from 1000 to 10,000 and a non-ionic surfactant, and the substrate is 4-methylumbelliferyl phosphate.

DETAILED DESCRIPTION OF THE INVENTION

Key to successful treatment of allergic conditions is the accurate identification of the offending allergen or allergens and the titration of the patient to determine the desensitization dosage. In general, reconstituted allergen extract is injected in sufficient quantity to cause major production of antigen-specific IgG (blocking antibody) and major production and/or activation of suppressor T lymphocytes. However, the quantity should not be sufficient to cause major allergic reaction. To the extent that antigen-specific IgE is produced at an increased level, it is critical that the IgG and suppressor IgE production be in such balance as to prevent allergic reaction.

The concentration and amount of the desensitization dosage are dependent upon many factors which are specific to the patient undergoing the allergic reaction. It is therefore necessary to titrate the patient to determine the proper dosage. A variety of standard techniques are available to carry out this procedure. Examples of traditional procedures are described in *Remington's Pharmaceutical Sciences,* supra, pp 1344–1352. However, the methods available prior to this invention have lacked the specificity and accuracy to be more than a rough approximation of the order of magnitude of the appropriate beginning dose range. Furthermore, they have not provided any efficient procedure to determine the total IgE level in a patient serum, and consequently, no efficient way to relate an allergen specific IgE level determination to total IgE levels. The PRIST test requires several days for completion and the TANDEM test requires a full day. In contrast, the test of this invention can be completed in as little as two hours with great accuracy.

The method of this invention provides the specificity and accuracy to determine a suitable desensitization dosage, particularly when the allergen used for desensitization and the allergen component of the diagnostic method have the same allergen profile and specificity. After identification of the offending allergen or allergens and quantification of the total IgE and allergen specific IgE levels, desensitization immunotherapy procedures are employed. The procedure normally used involves injecting into the patient gradually increased doses of the allergen, usually to maximum tolerated doses (doses not giving rise to major allergic response), at varying intervals to develop protection against the agents. With the method of this invention, more exact assessment of the suitable desensitization dose can be initially determined, making unnecessary the exacting procedures formerly required. The exact mechanisms of this treatment are not fully understood. Booster injections to maintain control of the allergic reactions are required at intervals of one to four weeks. Usually the doses required for booster injections are substantially greater than the maximum dose required for control of the initial allergic reaction.

The process of this invention comprises a first step of contacting an insoluble support having anti-IgE antibody adhering thereto with patient serum for a sufficient time to permit conjugation of anti-IgE antibody with IgE in the patient serum and then removing the patient serum from the support. In this procedure the patient serum is preferably undiluted prior to contact with the supported anti-IgE antibody. The incubation time should be sufficient to permit substantial conjugation to occur, the time being temperature dependent. Suitable incubation times are from 15 to 180 minutes at temperatures within the range of from 15° to 50° C., the preferred contact time being from 30 to 120 minutes at temperatures within the range of from 20° to 40° C.

The insoluble support having the anti-IgE antibody adhering thereto is an important aspect of this invention. Anti-IgE antibodies are available from many sources, and the methodology for producing them is well known and is described in several of the patents and publications cited above. The preferred antibodies are monoclonal antibodies. The technology for making monoclonal antibodies is well developed, and the procedures suitable for making monoclonal anti-IgE antibodies are described by D. Catty, et al in "Antisera in Immunoassays with special Reference to Monoclonal Antibodies to Human Immunoglobulins", *Immunoassay's for the 80's,* supra, pp 133–153 and the publications cited therein, the entire contents of which are hereby incorporated by reference.

A wide variety of compounds can be employed as the solid support, the primary consideration being the binding of the anti-IgE antibodies to the surface, the absence of interference with the enzyme labeled anti-IgE antibody reagent, enzymatic reaction thereof with a substrate and fluorescent properties of the enzymatic reaction product. Organic and inorganic polymers, both natural and synthetic can be employed as the solid support. Examples of suitable polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, styrene-acrylonitrile copolymers, rayon, nylon, polyvinylbutyrate, polyformaldehyde, etc. Other materials which can be employed as the insoluble support are silica gel, silicon wafers, glass, paper, insoluble protein, metals, metaleoids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12–24 carbon atoms) alkyl ammonium salts and the like.

The surface can, if desired, be polyfunctional or capable of being polyfunctionalized so as to allow for covalent bonding between the reagents and the surface. Functional groups which may be present on the surface and used for linking can include carboxylic acids, aldehydes, amino groups, cyano groups, ethylenic groups, hydroxyl groups, or mercapto groups and the like. The manner of linking antibodies to the various surfaces is well known and is amply illustrated in the literature, for example, "Immobilized Enzymes", Ichiro Chibata, Halsted Press, New York, 1978, and A. Cuatrecasas, *J. Bio. Chem.* 245, 3059 (1970).

The lengths of the linking group may vary widely depending upon the nature of the compound being linked, the effect of the distance between the linked compound and the surface on the linked compound's properties, the potential for cross-linking of the linked compound, and the like. The linking group may be a bond or have up to about 12, usually not more than 10 atoms in a chain. The linking group may be aliphatic, alicyclic, aromatic, heterocyclic, or combinations thereof. The total number of atoms in the linking group will not be more than about 20, usually not more than about 16 atoms other than hydrogen, which will be carbon, oxygen as oxy or oxo, both oxo-carbonyl and non-oxo-carbonyl, nitrogen as amino or amido, or sulfur as thio or thiono. Illustrative groups include methylenecarbonyl, succinimidyl, alpha-haloacetyl, thiomethylene, glycyl or polyglycyl, succindioyl, maledioyl, glutardialkylidene, methylenephenyldiazo, and ureido.

Preferred diagnostic supports of this invention comprises polystyrene, styrene copolymers including styrene-(vinyl monomer) copolymers such as styrene-acrylonitrile copolymers, polyolefins such as polyethylene and polypropylene, and acrylate and methacrylate polymers and copolymers. The anti-IgE antibody is preferably bound thereto by adsorption, ionic bonding, van der Waals adsorption, electrostatic bonding, or other non-covalent bonding. It can also be bound to the support by covalent bonding. A particularly advantageous support for this procedure comprises a microtiter plate having a plurality of wells. The well surface or plastic cup inserts therein can constitute the insoluble support. Most advantageously, the microtiter plate or the well inserts are opaque to light so that excitation light applied to a well or fluorescence generated in response thereto does not reach or influence contents of the surrounding wells. With this system each well can be employed as a test system independent of the other wells.

In a procedure for non-covalent adhesion of anti-IgE antibody to the surface of an insoluble support, the anti-IgE antibody can be applied to the surface of a support such as a polystyrene microtiter well or polystyrene individual insert well therefor, in an aqueous buffer solution. The surface is initially cleaned with a cleaning fluid such as methanol and dried. The buffered anti-IgE antibody solution is placed in the well or insert cup and incubated at room temperature until adsorption occurs, for example from 2 to 18 hours and preferably from 16-18 hours, at temperatures of from 4° to 40° C. and preferably from 20° to 26° C. The well is then rinsed with a weak saline solution and dried.

Procedures for covalently adhering anti-IgE antibodies to insoluble supports are described by Ichiro Chibata in *Immobilized Enzymes,* Halsted Press, New York, 1978, and by A. Cuatrecasas, *J. Bio. Chem.* 245, 3059 (1970), the entire contents of which are hereby incorporated by reference. The surface can be coated with a protein and coupled with anti-IgE antibody using the procedures described in U.S. Pat. No. 4,210,418 using glutaraldehyde as a coupling agent, for example. In a still further procedure, the well can be coated with a layer having free isocyanate groups such as a polyether isocyanate, and application of the anti-IgE antibody in aqueous solution thereto effects the requisite bonding. In a still further procedure, the anti-IgE antibodies can be coupled to a hydroxylated material by means of cyanogen bromide as described in U.S. Pat. No. 3,720,760.

In an alternate procedure, the support surface can be first coated with an inert protein. This procedure is described with respect to polyethylene or polystyrene tubes but is equally suitable for wells, beads, etc. To the reactive bottom part, in accordance with this procedure, is attached an inert protein. The term "inert protein" means a protein which does not take part in the immunochemical reaction and does not adversely affect the biological substance. The proteins that can be used are well known to those skilled in the art. They include any proteinaceous material such as serum albumins or globulins obtained from various animal species or can be other uniform materials. Particularly preferred are bovine gamma globulin and gelatin since these are readily available. The proteinaceous material employed should be sufficiently homogeneous so that an essentially continuous surface can be obtained by the use thereof. Such a surface is readily obtainable with the above proteins. Anti-IgE antibody is then bonded to the inert protein.

More specifically, the plastic surfaces are treated by a process which comprises (a) coating the surface by adsorption with an inert protein under adsorbing conditions, (b) attaching anti-IgE antibody to the inert protein coating, (c) treating the coupled part with a stabilizing agent to stabilize the anti-IgE antibody against denaturization, and (d) drying the reactive part under drying conditions that will not substantially denature the anti-IgE antibody.

The amount of inert protein required to give optimum results is dependent on the nature of the inert protein, the surface and the anti-IgE antibody. This amount is readily determinable by those skilled in the art. Typically, only a thin film (e.g., at least a thickness of one layer of molecules) of protein is attached to the surface. Generally, this is a sufficient amount to effect a uniform coating to which the biologically active substance may by attached.

The inert protein is readily attached to the surface to form a coating by spraying, soaking, or preferably by immersing the surface in an aqueous solution of inert protein such as an aqueous buffer solution under coating conditions. In this manner the protein is adsorbed to the surface. It is advantageous to use aqueous phosphate buffer solutions. Such buffers are described in U.S.P. XIX and are generally prepared using dipotassium hydrogen phosphate and potassium dihydrogen phosphate.

The inert protein is coated under adsorbing conditions which will not lead to denaturization of the protein. Specific pH and temperature conditions depend on the particular inert protein. Adsorbing conditions include conventional pH's, e.g. about 3 to 10 and conventional temperatures, e.g., about 20° C. to 30° C. While lower and higher application temperatures may be employed, for example as low as 4° C. and as high as 50° C., there is no significant advantage. In fact, at temperatures in excess of 50° C., the protein is generally denatured. At temperatures lower than 4° C. the protein is difficult to apply. For example, bovine gamma globulin is coated generally at a pH of 5 to 7 (optimally 6.4) at room temperature.

To facilitate attachment of the inert protein, the surface of the lower reactive part prior to attachment may be treated with solvents, surfactants, acids or bases. Surfactants, advantageously sodium dodecyl sulfate, are utilized as detergents to clean the surface and make it wettable. If the polymers contain carboxyl groups on the surface, it is often desirable to treat them with a salt-forming base, e.g. KOH, to convert them to the salt form, thus giving them a negative charge which provides for enhanced electrical attraction and greater adsorption. The base also helps to clean the surface. In another aspect, it is advantageous to make the charge distribution on the surface about equal to that of the inert protein to be applied. This is accomplished by washing the surface with an aqueous buffer solution having about the same pH as the coating solution containing the inert protein prior to coating.

The anti-IgE antibody can be attached by any suitable means. Such suitable means known to the art include adsorption, covalent binding, ionic binding and entrapment. Methods for covalently binding the anti-IgE antibody to the inert protein are disclosed in U.S. Pat. Nos. 3,553,310 and 3,639,558, which are hereby incorporated by reference. A preferred method of covalent binding to inert protein comprises first treating the protein with an aldehyde coupling agent, followed by application of the anti-IgE antibody under conditions which permit the aldehyde to covalently bind to both the inert protein and the anti-IgE antibody. Suitable aldehyde coupling agents are those which have either ethylenic unsaturation or a plurality of aldehyde groups, or both, such as acrolein, methacrolein and 2-butenal. Dialdehydes can be employed such as glutaraldehyde, propanedial and butanedial.

When one of these aldehydes is contacted with the surface of the inert protein, the protein is stabilized and polymerized by cross-linking, and aldehyde active moieties are fixed to the surfaces. These moieties are believed to be carbonyl groups and are highly reactive to the amine groups of anti-IgE antibodies since they form covalent bonds between the protein particles and the antibodies.

The aldehyde or ethylenically unsaturated coupling procedures can also be used to covalently bond anti-IgE antibodies to other surfaces having primary amino groups. For example, polylysine coated polystyrene can be coupled to anti-IgE antibodies with glutaraldehyde.

Alternative to aldehydes, there may be used other coupling moieties such as compounds having two or more of the following reactive groups: azo, sulfonic acid or fluoro groups activated by nitro groups, azide, imine or reactive chloro groups connected to a ring having appropriate resonance structure. These reactive groups are capable of reacting with the primary amino, sulfylhydryl, carboxylic, hydroxyl and phenolic groups in the substances constituting the inert protein as well as the anti-IgE antibodies to be coupled thereto.

A representative list of such coupling agents is bis-diazobenzadine, disulfonic acid, tetraazo-p-phenylenediamine difluorodinitrobenzene, difluorodinitrophenylsulfone, carbodiimides, toluene diisocyanate, cyanuric chloride, dichlorotriazine, N-t-butyl-5-methylisoxazolium perchlorate. Carbodiimides which can be employed are N,N-dicyclohexylcarbodiimide, 1-ethyl-3(3-dimethylaminopropyl)carbodiimide hydrochloride, and 1-cyclohexyl-3(2-morpholinyl(4)-ethylcarbodiimide)metho-p-toluene sulfonate.

Alternatively the anti-IgE antibodies can be attached by adsorption according to the procedure described in U.S. Pat. No. 3,551,555. The solid support surface can also be coated with a material which will bind to the anti-IgE antibodies through an isocyanate bond such as that provided by polyether isocyanate coatings (HYPOL-2000, W.R. Grace & Co., Lexington, Mass.).

Procedures for binding reagents to glass surfaces are known in the art and are described in U.S. Pat. No. 4,280,992, for example. Methods used of binding the anti-IgE antibodies to the glass are not critical. Frosted glass is preferred. Anti-IgE antibodies may be bound to the glass surface by physical or chemical methods. The latter are preferred when firm and permanent binding of a large amount of anti-IgE antibodies to the glass is desired.

Binding by a physical method can be attained mainly by physical adsorption (van der Waals adsorption). Thus, the glass may be dipped in a solution of the anti-IgE antibodies and incubated, or allowed to stand, for an appropriate period of time to form physical binding. The solution can have a concentration of generally 0.01 to 400 g per liter and preferably 0.1 to 1.0 g per liter. The dipping or immersion treatment can be carried out, for example, at a temperature of 0° to 45° C. for one to 48 hours.

As a suitable chemical method, the anti-IgE antibodies can be bound to glass surfaces, and preferably frosted glass surfaces, with the aid of a silane coupling agent, and if necessary, a cross-linking agent. There may be used any silane coupling agent having in its molecule both a functional group reactive with the glass and a functional group reactive with the anti-IgE antibodies and/or the cross-linking agent. Examples of suitable functional groups reactive with the glass include those reactive with a silanol group of the glass, and include, for example, alkoxysilyl groups (such as methoxy or ethoxy-substituted silyl groups), and the like. Examples of suitable functional groups reactive with the anti-IgE antibodies and/or the cross-linking agent are those reactive with amino, carboxyl and/or thiol group(s), and include, for instance, carboxyl, epoxy, haloalkyl (such as chloroethyl and chloropropyl), aldehyde, primary and secondary amino, thiol, isocyanate, carboxylate, imino and nitrile (or cyano) groups, and the like. More specifically, examples of suitable functional groups reactive with the amino group are carboxyl, epoxy, haloalkyl and aldehyde groups. Suitable functional groups reactive with the carboxyl group include, for example, primary and secondary amino, and epoxy groups. Suitable functional groups reactive with the thiol group include thiol, epoxy, haloalkyl and aldehyde groups, and the like.

In binding the anti-IgE antibodies to the glass, the silane coupling agent may be used with or without the cross-linking agent. The cross-linking agent may be selected according to the kind of the silane coupling agent and the kind of the anti-IgE antibodies to be bound. There may be used any cross-linking agent which can cross-link the silane coupling agent with the anti-IgE antibodies. As such cross-linking agent there may be mentioned, those compounds that can cross-link the amino, carboxyl or thiol group of the silane coupling agent with the amino, carboxyl or thiol group of the immunologically active substance, such as those capable of producing a cross-linkage between the thiol group and the thiol group, or between the amino group and the thiol group. Examples of suitable compounds which can cross-link between amino groups are aliphatic dialdehydes (such as glyoxal, malonaldehyde, succinaldehyde, glutaraldehyde) and dichlorotriazines (such as 2-amino-4,6-dichloro-s-triazine), and the like. Suitable cross-linking agents between thiol groups are, for instance, dimaleimide compounds (such as N,N'-o-phenylenedimaleimide, N,N'-m-phenylenedimaleimide). Suitable cross-linking agents between the amino group and the thiol group are exemplified by maleimidocarboxyl-N-hydroxysuccinimide esters (such as m-maleimidobenzoyl-N-hydroxysuccinimide ester, and 4-(maleimidomethyl)cyclohexane-1-carboxyl-N-hydroxysuccinimide ester).

Adsorbents useful in the process of the invention as solid supports for anti-IgE antibodies are known in the art. Suitable materials are listed below:

ADSORBENTS AND ABSORBENTS

Non-ionic cellulose
   e.g., Whatman (Clifton, N.J., U.S.A.) types—
     CF-1 ®, long fiber powder
     CF-11 ®, medium fiber powder
     CC-31 ®, microgranular powder
     CC-41 ®, microgranular powder
   e.g., Bio-Rad (Richmond, Calif., U.S.A.) types—
     Cellex ® N-1, powder
     Cellex ® 410, powder
Silica gel
   e.g., Whatman type—SG 81, loaded paper; or Bio-Rad types—Bio-Sil ® A or Bio-Sil ® HA
Hydroxylapatite (Bio-Rad)

Alumina; acid, base, or neutral types (Bio-Rad)
Alumina C-gamma gel (Bio-Rad)
Calcium phosphate
Hydroxypropl dextran
    e.g., Pharmacia (Piscataway, N.J., U.S.A.) type—Sephadex ® LH 20
Dextran (Pharmacia)
Dextran sulfate (Pharmacia)
Alkyl Agaroses
    e.g., Pharmacia types—octyl-Sepharose ® C1-4B or phenyl-Sepharose ® C1-4B
    e.g., Miles Research Products (Elkhart, Ind., U.S.A.) types—ω-amino alkyl agaroses
Lectin-agarose (Miles Research Products)
Poly-L-lysine agarose (Miles Research Products)
Plastics, e.g., polystyrene, polyethylene, and polypropylene

ANION EXCHANGE MATERIALS

Diethylaminoethyl (CEAE) cellulose
    e.g., Whatman types—
        DE-1 ®, floc
        DE-11 ®, powder
        DE-22 ®, fibrous
        DE-23 ®, fibrous
        DE-32 ®, dry, microgranular
        DE-52 ®, wet, microgranular
        DE-81 ®, paper
    e.g., Bio-Rad type—Cellex ® D, fibrous
Diethylaminoethyl (DEAE) agarose
    e.g., Bio-Rad type—DEAE Biogel ® A
Diethylaminoethyl (DEAE) dextran
    e.g., Pharmacia type—DEAE Sephadex ®, bead
Aminohexyl-Sepharose ® 4B (Pharmacia)
Ecteola cellulose
    e.g., Whatman types—
        ET-11 ®, powder
        ET-41 ®, powder (high purity)
        ET-81 ®, paper
    e.g., Bio-Rad type—Cellex ® E, fibrous
Triethylaminoethyl (TEAE) cellulose
    e.g., Bio-Rad type—Cellex ® T, fibrous
Diethyl-(2-hydroxypropyl)-amino (QAE) cellulose
    e.g., Bio-Rad type—Cellex ® QAE, fibrous
Diethyl-(2-hydroxypropyl)-amino (QAE) dextran
    e.g., Pharmacia type—QAE-Sephadex ®
Benzolyated diethylaminoethyl cellulose
    e.g., Bio-Rad type—Cellex ® BD, fibrous

CATION EXCHANGE MATERIALS

Cellulose phosphate
    e.g., Whatman types—
        P-1 ®, floc
        P-11 ®, powder
        P-41 ®, powder (high purity)
        P-81 ®, paper
Carboxymethyl cellulose
    e.g., Whatman types—
        CM-1 ®, floc
        CM-11 ®, powder
        CM-22 ®, fibrous
        CM-23 ®, fibrous
        CM-32 ®, dry, microgranular
        CM-52 ®, wet, microgranular
        CM82 ®, paper
    e.g., Bio-Rad type—Cellex ® CM, fibrous
Carboxymethyl dextran
    e.g., Pharmacia type—CM-Sephadex ®
Phosphoryl cellulose
    e.g., Bio-Rad type—Cellex ® P, fibrous
Carboxymethyl agarose
    e.g., Bio-Rad type—CM Biogel ® A
    e.g., Pharmacia type—CH-Sepharose ® 4B
Sulphopropyl dextran
    e.g., Pharmacia type—SP-Sephadex ®

Reagents formed by chemically coupling or combining the anti-IgE antibodies to polymeric carrier particles of varying particle size are well-known, e.g., U.S. Pat. Nos. 3,882,225; 3,957,931; 3,825,525; 3,629,558; 3,565,987, 3,553,310; 3,407,076; 3,236,732; 3,096,250; 4,092,114; 4,140,662; 4,210,723; 4,226,747; 4,259,313; 3,088,875; 3,766,013; 3,619,371; 3,809,613; 3,853,987; 3,963,441; 3,551,555; and 3,649,346. Netherlands Pat. No. 7,201,308; and British Pat. No. 1,257,263.

When covalent bonding of the anti-IgE antibodies to the polymer bead is desired, it is preferred to use for the bead a monomer which, after bead formation, retains a group which can react with amino, amido, or sulfonamido groups on the anti-IgE antibodies to be bound to the bead, e.g. chlorobenzyl, chloroacetyl, chloroethylcarbonyl, chloroethylsulfonyl, acryloyl, or vinyl-sulfonyl group.

Also the surface groups can be bonded to anti-IgE antibodies through bifunctional-linking groups reacted with the reactive bead surface group and with the anti-IgE antibodies.

The beads are usually prepared by polymerizing one or more vinyl monomers by standard procedures. Suitable vinyl monomers which can be polymerized and/or copolymerized with each other in any proportions and/or with other monomers to yield the desired beads include monovinylidene carboxylic monomers, e.g., styrene, alphamethylstyrene, ar-(t-butyl)styrene, ar-methylstyrene, ar,ar-dimethylstyrene, ar-chlorostyrene, ar-(t-amyl) styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of alpha, beta-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; alpha, beta-ethylenically unsaturated esters of non-polymerizable carboxylic acids, e.g., vinyl benzoate, vinyl toluate ar-ethylbenzoate, allyl ar-ethylbenzoate, vinyl trimethylacetate, vinyl pivalate, vinyl trichloroacetate and other such monomers wherein the unsaturated moiety has from 2 to 14 carbon atoms and the acid moiety has from 2 to 12 carbon atoms; alpha, beta-ethylenically unsaturated nitriles, e.g., such as nitriles having not more than 12 carbon atoms; other polymerizable vinyl monomers such as vinyl chloride, vinyl bromide and the like.

In the preferred procedure, the anti-IgE antibody on the insoluble support such as a well surface is stabilized with an aqueous buffer solution which forms an animal protein-saccharide complex on the well surface. A preferred buffer solution contains from 0.05 to 1.0 weight percent water-soluble animal protein. Suitable water-soluble proteins include bovine serum albumins of bovine (BSA), human (HSA), rabbit (RSA), goat (GSA), sheep (SSA), horse (HOSA), etc.; serum gamma-globulin of the previously described animals; and other animal proteins such as ovalbumin, fibrinogen, thrombin, transferin, glycoproteins, etc. The preferred water-soluble animal protein is bovine serum albumin. The solution also contains from 0.1 to 5 weight percent of one or more water-soluble saccharides. Suitable saccharides include sorbitol, sucrose, maltose, cellobiose, lactose, manitose, annylose and the like. A preferred saccharide is sucrose. The solution contains sufficient phosphate to constitute a 0.01 to 0.5M phosphate buffer (PBS) solution having a pH of from 6 to 8 and a preservative such as from 0.01 to 0.1 weight percent sodium azide.

The first step of the method of this invention is preferably preceded by a prerinse step. In the prerinse step, the support surface is contacted with an aqueous buffered rinse solution containing from 0.0001 to 0.5 weight percent of water-soluble protein. This prerinse step is particularly advantageous when the water-soluble polymer is water-soluble animal protein. A preferred rinse solution of this invention is an aqueous phosphate buffer solution having a phosphate molarity of from 0.0001 to 0.05, a pH of from 6 to 8 and containing from 0.001 to 0.1 weight percent non-ionic surfactant and from 0.0001 to 0.5 weight percent of water-soluble protein. Suitable non-ionic surfactants include polyoxyethylene ethers (BRIJ ®) such as lauryl, cetyl, oleyl, stearyl, and tridecyl polyoxyethylene ethers; polyoxyethylenesorbitans (TWEEN ®) such as polyoxyethylenesorbitan monolaurate, monopalmitate, monostearate, monoleate and trioleates; and other polyoxyethylene ethers (TRITON ®), for example. A preferred non-ionic surfactant is octylphenoxypolyethoxy ethanol having 40 ethylene oxide units (TRITON X-405, Rohm and Haas Company). Suitable water-soluble proteins include bovine serum albumins of bovine (BSA), human (HSA), rabbit (RSA), goat (GSA), sheep (SSA), horse (HOSA), etc.; serum gamma-globulin of the previously described animals; and other animal proteins such as ovalbumin, fibrinogen, thrombin, transferin, glycoproteins, etc.

The buffer solution is advantageously prepared from a reagent concentrate of the invention comprising from 0.005 to 2.5 weight percent of the animal protein, from 0.5 to 5 weight percent non-ionic surfactant, from 10 to 20 weight percent sodium chloride, from 015 to 5 weight percent stabilizer and sufficient phosphate salt to provide for a 0.02 to 0.05M phosphate solution. The pH can be from 6 to 8. The preferred buffer concentrate contains about 0.5 weight percent of the animal protein, 0.1 weight percent TRITON X-405 non-ionic surfactant, 17 weight percent sodium chloride, and 2 weight percent sodium azide, 0.01M phosphate and has a pH of 7.4.

After conjugation of serum IgE with anti-IgE antibody adhering to the insoluble support has occurred, the patient serum is removed therefrom. Surplus liquid is removed and the solid surface is then rinsed with a suitable rinse solution such as that described above.

The second step of the process of this invention comprises contacting the insoluble support with an anti-IgE antibody labeled with a fluorogenic enzyme. The incubation is continued for sufficient time to permit serum IgE (if any) conjugated with anti-IgE antibody on the insoluble support to conjugate with the enzyme labeled anti-IgE antibody. After incubation, the excess liquid is removed, and the surface of the insoluble support is rinsed with a weak saline solution as described above with respect to the first step to remove unconjugated antibody. Preferably the support is rinsed with the preferred rinse solution of this invention described above.

The anti-IgE antibodies can be the same or different from those described above and are preferably monoclonal antibodies.

Fluorogenic enzymes and methods for bonding them to anti-IgE antibodies without impairing the ability of the antibody to selectively conjugate with IgE are well known in the art. Suitable enzymes and procedures for coupling them to antibodies are described in U.S. Pat. No. 4,190,496, for example, the contents thereof being hereby incorporated by reference. The preferred fluorogenic enzymes and the suitable substrates corresponding thereto include horse-radish peroxidase for which a suitable substrate is homovanillic acid or 4-hydroxy-3-methoxyphenylacetic acid, beta-galactosidase for which a suitable substrate is 4-methylumbelliferyl-beta-D-Galactoside, alkaline phosphatase for which a suitable substrate is 4-methylumbelliferyl phosphate and other umbelliferyl phosphates such as 4-carboxyumbellifery phosphate, and umbelliferyl phosphate 4-carboxy alkylesters, etc.

Examples of suitable procedures for enzyme labeling the anti-IgE antibody include use of carbodiimides, dialdehyde, and bifunctional coupling reagents as described in covalent linkage of anti-IgE antibody to protein. Preferably the coupling agent is a carbodiimide such as 1-ethyl-3-(3-N,N-dimethylaminopropyl)carbodiimide hydrochloride and 1-cyclohexyl-3(2-morpholinoethyl) carbodiimide methyl-p-toluenesulfonate. Other suitable coupling agents include aldehyde coupling agents having either ethylenic unsaturation such as acrolein, methacrolin, or 2-butenal or having a plurality of aldehyde groups such as glutaraldehyde, propanedial or butanedial. Other coupling agents include bifunctional NHS-esters such as disuccinimidyl suberate, disuccinimidyl tartarate, bis[2-(succinimidooxycarbonyloxy)ethyl]sulfone, disuccinimidyl (N,N'-diacetylhomocystine, dithiobis(succinimidyl propionate), ethylene glycolbis(succinimidyl succinate); heterobifunctional reagents such as N-5-azido-2-nitrobenzoyloxy succinimide, p-azidophenacyl bromide, p-azidophenylglyoxal, 4-fluoro-3-nitrophenyl azide, N-hydroxysuccinimidyl-4-azidobenzoate, m-maleimidobenzoyl N-hydroxysuccinimide ester, methyl-4-azidobenzoimidate.HCl, p-nitrophenyl 2-diazo-3,3,3-trifluoropropionate, N-succinimidyl-6(4'-azido-2'-nitrophenylamino)hexanoate, succinimidyl 4-(N-maleimido-methyl)cyclohexane-1-carboxylate, succinimidyl 4-(p-maleimidophenyl)butyrate, N-succinimidyl (4-azidophenyldithio)propionate, N-succinimidyl 3-(2-pyridyldithio)propionate, N-(4-azidophenylthio)phthalimide, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate; and bifunctional imidoesters such as dimethyl adipimidate.2HCl, dimethyl suberimidate, dimethyl 3,3'-dithiobispropionimidate.2HCl, 2-iminothiolane.HCl. Covalent bonding of enzyme to the anti-IgE antibody can be carried out with the above reagents by conventional, well-known reactions, for example in the aqueous solutions at a neutral pH, at temperatures of less than 10° C. for 18 hours or overnight.

The enzyme labeled anti-IgE antibody is applied to the insoluble support in an aqueous solution. The solution preferably contains suitable salts and buffers to preserve the reactants and facilitate the conjugation reaction. For example, the solution can contain bovine serum albumin (BSA), phosphate buffer solution (PBS), and a mild surfactant such as a polyoxyethylene sorbitan ester employed in the rinse solutions described above. The rinse solutions described herein can also be used.

A preferred solution of this invention comprises from 0.1 micrograms per ml to 5 micrograms per ml and preferably from 1 microgram per ml to 2 microgram per ml anti-IgE antibody in an aqueous phosphate buffered solution having a phosphate molarity of from 0.0001 to 0.1 and preferably from 0.005 to 0.05 and a pH of from 6.0 to 8.0 and preferably 7.2 to 7.6. A critical ingredient in the anti-IgE solution is polyethylene glycol having molecular weights of from 1000 to 8000 and preferably from 2000 to 4000 in concentrations of from 1 to 8 and preferably from 2 to 6 weight percent. Polyethylene glycols greatly increase the speed and sensitivity of the reaction. Another important ingredient is a non-ionic surfactant in concentrations of from 0.001 to 0.5 and preferably from 0.02 to 0.1 weight percent. Suitable non-ionic surfactants include those described above with respect to rinse solutions, for example. A preferred non-ionic surfactant is TRITON X-405. The surfactant surprisingly reduces the non-specific background fluorescence signal in the assay.

With the preferred anti-IgE solutions of this invention, the incubation time of the solutions with the insoluble support is temperature dependent. At temperatures of 15° to 40° C., incubation times of at least from 15 to 180 minutes can be used. The preferred temperatures are within the range of from 20° to 30° C., and at these temperatures, incubation times from 30 to 120 minutes can be employed. It should be appreciated that prolonged incubation times in any of the steps of this invention can reduce the efficacy of the process. Since rapid analysis is an objective of this invention, the lowest times which still yield the desired accuracy are preferred.

The solid support is then rinsed to remove residual, unconjugated enzyme labeled anti-IgE antibody. The rinse solutions described above are suitable.

The third step of the process of this invention comprises contacting the solid support with a solution of a substrate which undergoes chemical reaction in the presence of the fluorogenic enzyme for a time sufficient for fluorescent compounds to be formed. Suitable substrates and the enzymes they are converted by are known in the art and are described in U.S. Pat. No. 4,190,496, for example. Examples of substrates have been described hereinabove with respect to the corresponding fluorogenic enzyme.

The solid is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reacion product to form. At temperatures of from 18° to 40° C., incubation times of from 5 to 240 minutes can be used. Preferably, the temperature is within the range of from 20° to 26° C., and the incubation time is from 30 to 90 minutes.

The fluorescence level in the solution is then measured. The equipment and procedures for determining the level of fluorescence in the substrate solutions are those conventionally employed in the art. The level of fluoresence is a function of the enzyme concentration on the insoluble support which is, in turn, a function of the IgE antibody level in the patient serum. By comparing the fluoresence level with the levels measured by carrying out the procedure with control solutions containing known concentrations of IgE antibody, the precise concentration of the corresponding IgE antibody in the patient serum can be determined.

Suitable fluorometers are the fluorometers by Perkin-Elmer, American Instrument Company, and Turner Designs. The Allergenetics Fluorometer (Allergenetics, Inc., Mountain View, Calif.) is preferred.

This invention is further illustrated by the following specific but non-limiting examples. Temperatures are given in degrees Centigrade and concentrations are given as weight percents unless otherwise specified.

EXAMPLE 1

To a microtiter plate made of opaque polystyrene is added 100 microliters of a solution of total anti-human IgE monoclonal antibody prepared according to a modified procedure of M. O'Sullivan, et al, *Analytical Biochem.* 100, 100 (1979). The monoclonal antibody is applied in a solution of 0.1M phosphate buffered solution, pH 8.5, with 0.1 wt. % sodium azide preservative.

The coating process is allowed to proceed at room temperature for 2 hours (or overnight). At the end of the coating process, the liquid in each well is removed by aspiration, and the support is air-dried at room temperature for one hour.

The well is then contacted with a 0.1M phosphate buffer solution (PBS), pH 7.4, containing 2.5 wt. % sucrose, 0.25 wt. % bovine serum albumin, 0.05 wt. % sodium azide and TRITON X405 for 30 min, the excess is removed, and the well vacuum dried and sealed. The well thus coated can be used for assaying patient serum for total IgE antibody.

EXAMPLE 2

A microtiter plate well product of Example 1 to which anti-IgE antibody is adhered is contacted with patient serum containing IgE antibody and incubated for one hr. The serum is removed, and the well washed three times with a buffered rinse solution containing 0.85 wt. % sodium chloride, 0.05 wt. % TRITON X405 and 0.1 wt. % sodium azide preservative in a 0.01 aqueous phosphate buffer solution, pH 7.2. Serum IgE specific antibody is conjugated to the microtiter plate well surface.

The microtiter plate well is then contacted for 30 min with 100 microliters of a solution of alkaline phosphatase conjugated anti-human IgE monoclonal antibody prepared according to a modified procedure of M. O'Sullivan, et al, *Analytical Biochem.*, vol. 100, page 100 (1979). The monoclonal antibody is applied in a solution of 0.01M phosphate buffered saline, pH 7.2, containing 4 wt. % polyethylene glycol having a molecular weight of 4000 (PEG 4000), 0.05 wt. % TRITON X-405, and 0.1 wt. % sodium azide preservative. The alkaline phosphatase conjugated anti-human IgE monoclonal antibody solution is removed from the microtiter plate well, and it is rinsed three times with the buffered rinse solution described above.

To the microtiter plate well is then added 100 microliters of a substrate solution containing $10^{-4}$M 4-methyl umbelliferyl phosphate in 1.25M 2-amino-2-methyl-propanol, pH 9.5 in deionized water containing 0.125 mM magnesium chloride and 0.1 wt. % sodium azide. After 30 minutes, the fluorescence level is read with a fluorometer with the excitation at 365 nm and the reading at 450 nm. By comparing the reading with levels measured by repeating the procedure with control solutions having known concentrations of total IgE antibody, the total IgE level in the patient serum is determined.

EXAMPLE 3

A microtiter plate well product of Example 1 (to which an anti-IgE antibody is adhered) is rinsed for 5 minutes with a buffered rinse solution containing 0.85 wt. % sodium chloride, 0.05 wt. % TRITON X405, 0.01 wt. % BSA, and 0.1 wt. % sodium azide preservative in a 0.01 aqueous phosphate buffer solution, pH 7.2, and the surplus is removed. The prerinsed microtiter plate is then contacted with patient serum containing IgE antibody and incubated for one hr. The serum is removed, and the well washed three times with the buffered rinse solution.

The buffered rinse solution is prepared by diluting the following concentrate with 50 parts by volume distilled or deionized water to one part by volume concentrate:

| | |
|---|---|
| Bovine serum albumin | 0.5 wt. % |
| Non-ionic surfactant (TRITON X-405) | 0.1 wt. % |
| Sodium Chloride | 17 wt. % |
| Sodium azide | 2 wt. % |
| Sodium phosphate | 0.05 M |
| pH adjusted to | 7.4 |

Serum IgE antibody is conjugated to the microtiter plate well surface.

The microtiter plate well is then contacted for 30 min with 100 microliters of a solution of alkaline phosphatase conjugated anti-human IgE monoclonal antibody prepared according to a modified procedure of M. O'-Sullivan, et al, *Analytical Biochem.*, vol. 100, page 100(1979). The monoclonal antibody is applied in a solution of 0.01M phosphate buffered saline, pH 7.2, containing 4 wt. % polyethylene glycol having a molecular weight of 4000 (PEG 4000), 0.05 wt. % TRITON X-405, 0.01 wt. % BSA, and 0.1 wt. % sodium azide preservative. The alkaline phosphatase conjugated anti-human IgE monoclonal antibody solution is removed from the microtiter plate well, and it is rinsed three times with the buffered rinse solution described above.

To the microtiter plate well is then added 100 microliters of a substrate solution containing $10^{-4}$M 4-methyl umbelliferyl phosphate in 1.25M 2-amino-2-methyl-propanol, pH 9.5 in deionized water containing 0.125 mM magnesium chloride and 0.1 wt. % sodium azide. After 30 minutes, the fluorescence level is read with a fluorometer with the excitation at 365 nm and the reading at 450 nm. By comparing the reading with levels measured by repeating the procedure with control solutions having known concentrations of total IgE antibody, the serum total IgE level in the patient serum is determined.

The invention claimed is:

1. A method for identifying and quantifying total IgE levels in patient serum comprising
    (a) contacting an insoluble support having anti-IgE antibody adhering thereto with patient serum for a sufficient time to permit conjugation and removing the patient serum therefrom;
    (b) contacting the insoluble support with anti-IgE antibody labeled with a fluorogenic enzyme for a time between 15 and 180 minutes and sufficient to conjugate label anti-IgE to any IgE present and removing unconjugated enzyme labeled anti-IgE antibody therefrom;
    (c) contacting the insoluble support with a solution of a substrate which undergoes reaction in the presence of the fluorogenic enzyme to yield fluorescent product for a period between 5 and 240 minutes;
    (d) measuring the fluorescence level in the solution; and
    (e) determining the total IgE level of the patient serum by comparing the fluorescence level measured with those of control solutions.

2. The method of claim 1 wherein the insoluble support is contacted in step (b) with enzyme labeled anti-IgE antibody in an aqueous solution containing from 0.01 to 0.1 wt. % of a non-ionic surfactant.

3. The method of claim 1 wherein the patient serum is removed from the insoluble support in step (a) by rinsing with a phosphate buffered solution having a pH within the range of from 6 to 8 and containing a non-ionic surfactant.

4. The method of claim 1 wherein the unconjugated anti-IgE antibody is removed from the insoluble support in step (b) with a phosphate buffered solution having a pH within the range of from 6 to 8 and containing a non-ionic surfactant.

5. The method of claim 1 comprising
    (a) contacting an opaque polystyrene or styrene-(vinyl monomer) copolymer support having an anti-IgE antibody adhering thereto with patient serum for a sufficient time to permit conjugation of serum IgE antibody thereto;
    (b) removing residual patient serum from the support;
    (c) contacting the support with an anti-IgE antibody labeled with a fluorogenic enzyme in an aqueous solution containing polyethylene glycol and a non-ionic surfactant for a time between 15 and 180 minutes and sufficient to permit conjugation of anti-IgE antibody to any allergen specific IgE conjugated to the support;
    (d) removing residual aqueous solution from step (c), immediately above, from the support;
    (e) contacting the support with a solution of a substrate which undergoes reaction in the presence of the fluorogenic enzyme to yield fluorescent product for a time between 5 and 240 minutes;
    (f) measuring the fluorescence level of the solution; and
    (g) determining the total IgE level of the patient serum by comparing the fluorescence level measured in with those of control solutions.

6. The method of claim 1 wherein the insoluble support having anti-IgE anbtibody adhering thereto has been treated with an aqueous buffer solution containing water-soluble saccharide and water-soluble animal protein.

7. The method of claim 1 wherein the insoluble support comprises a plurality of reaction wells separated by opaque material.

8. The method of claim 1 wherein the insoluble support is prerinsed with an aqueous buffered solution containing from 0.0001 to 0.5 wt. % of animal protein before being contacted with patient serum.

9. The method of claim 8 wherein the soluble animal protein is bovine serum albumin.

10. The method of claim 1 wherein the insoluble support is a microtiter plate having wells made of opaque material.

11. The method of claim 10 wherein the anti-IgE antibody is a monoclonal antibody.

12. The method of claim 10 wherein the wells are made of polystyrene or a styrene-(vinyl monomer)-copolymer.

13. The method of claim 10 wherein the anti-IgE antibody is labeled with alkaline phosphatase.

14. The method of claim 13 wherein the substrate is 4-methylumbelliferyl phosphate.

* * * * *